United States Patent
Dubief et al.

[11] Patent Number: 6,024,946
[45] Date of Patent: Feb. 15, 2000

[54] SILICON AND LATEX-BASED COMPOSITION FOR THE TREATMENT OF KERATINOUS SUBSTANCES

[75] Inventors: Claude Dubief, Le Chesnay; Danièle Cauwet, Paris, both of France

[73] Assignee: L'Oreal, Paris, France

[21] Appl. No.: 08/892,202

[22] Filed: Jul. 14, 1997

Related U.S. Application Data

[62] Continuation of application No. 08/609,488, Mar. 1, 1996, abandoned, which is a continuation of application No. 08/162,007, filed as application No. PCT/FR92/00485, Jun. 2, 1992, abandoned.

[30] Foreign Application Priority Data

Jun. 3, 1991 [FR] France .................. 91 06657

[51] Int. Cl.[7] ................ A61K 7/06; A61K 7/11
[52] U.S. Cl. ............... 424/70.1; 424/70.12; 424/70.15; 424/70.16; 424/47; 424/70.11; 424/70.17; 424/78.03
[58] Field of Search .............. 424/70.1, 70.15, 424/70.12, 70.16, 47

[56] References Cited

U.S. PATENT DOCUMENTS

| | | | |
|---|---|---|---|
| 4,963,348 | 10/1990 | Bolich | 424/71 |
| 5,104,642 | 4/1992 | Wells | 424/47 |
| 5,120,531 | 6/1992 | Wells | 424/70 |

FOREIGN PATENT DOCUMENTS

| | | |
|---|---|---|
| 0214626 | 5/1988 | European Pat. Off. . |
| 0266921 | 5/1988 | European Pat. Off. . |
| 0424260 | 4/1991 | European Pat. Off. . |
| 2114580 | 8/1983 | United Kingdom . |

*Primary Examiner*—Thurman K. Page
*Assistant Examiner*—Lakshmi Channavajjala
*Attorney, Agent, or Firm*—Jacobson, Price, Holman & Stern, PLLC

[57] ABSTRACT

Compositions for the treatment of keratinous substances, containing, in an aqueous medium, at least one silicone and at least one latex in soluble in the aqueous medium, and at least one agent for suspending silicone and latex and/or at least one thickening agent selected from guar gum, acacia gum, scleroglucans, polyacrylic acids, crosslinked or not, aqueous dispersions of crosslinked ammonium acrylate/ acrylamide copolymers and an emulsion of the neutralized 2-methylpropane sulphonic acrylamide/ acrylamide copolymer.

21 Claims, No Drawings

SILICON AND LATEX-BASED COMPOSITION FOR THE TREATMENT OF KERATINOUS SUBSTANCES

This application is a continuation of application Ser. No. 08/609,488, filed Mar. 1, 1996, abandoned, which in turn is a continuation of application Ser. No. 08/162,007, filed May 2, 1994, abandoned. This is a 371 of PCT/FR92/00485, filed Jun. 2, 1992.

The present invention relates to a composition for treatment of keratinous materials, in particular hair, containing a silicone, a latex and a suspension agent for the latex and the silicone and/or a thickening agent, to methods for their use and in particular to a cosmetic treatment using this composition.

Hair is well known to be damaged and weakened by the action of external atmospheric influences such as light and bad weather, also by mechanical or chemical treatment, such as brushing, combing, heat, permanent waving, dyeing and bleaching.

In certain cases, it is go damaged that splits are formed in the hair ends; these split ends are due to longitudinal breaks in the fibre, particularly near the tips. The hair then becomes rough and difficult to comb through.

There is thus a need for compositions for treating keratinous fibres to restructure the damaged fibres as best as possible and render them smooth and easily corked through. There is also a need for this effect to be maintained over a prolonged period and thus avoid too frequent repetition of the treatment which could render the hair dull.

It has been discovered by the applicant that an association of a silicone, a latex and a suspension agent for the latex and the silicone and/or a thickening agent can repair the hair fibre and endow it with softness, ease of combthrough and a smooth, coated feel.

The applicant has also been discovered that the effects of the association of a silicone, a latex and a suspension agent for the latex and the silicone and/or a thickening agent persist when compared with compositions containing only silicone, and improve combthrough, which persists longer, even after one or more, shampoos, compared with compositions containing only silicone or latex.

The specific thickening agents and/or suspension agents defined below result in regular distribution of the silicones and the latex as a homogeneous suspension in the composition. They also enable the composition to be easily applied to keratinous material.

The effects described above have been found to persist even after several shampoos.

The invention consists in a composition for treatment of keratinous material comprising, in an appropriate medium for such application, at least one silicone, at least one latex and at least one suspension agent for the silicone and the latex and/or at least one thickening agent selected from guar gum, gum arabic, scleroglucanes, polyacrylic acids which may or may not be crosslinked, aqueous dispersions of crosslinked ammonium acrylate/acrylamide copolymers and an emulsion of neutralised acrylamide/2-methylpropane sulfonic acrylamide copolymer.

The invention also consists in a treatment method for keratinous material, in particular hair or eyelashes, using a composition as defined below.

Further objects of the invention will become apparent from the following description and examples.

A composition for treatment of keratinous material in accordance with the invention is characterized in that it contains in an aqueous medium at least one silicone, at least one latex which is insoluble in the aqueous medium and a suspension agent for the silicone and the latex and/or at least one thickening agent selected from guar gum, gum arabic, scleroglucanes, polyacrylic acids which may or may not be crosslinked, aqueous dispersions of crosslinked ammonium acrylate/acrylamide copolymers and an emulsion of neutralized acrylamide/2-methylpropane sulfonic acrylamide copolymer.

Silicones for use in the present invention are polyorganosiloxanes which may be insoluble or soluble in aqueous media, and may be in the form of oils, waxes, gums or resins.

Polyorganosiloxanes are described in more detail in "Chemistry and Technology of Silicones" (1968) by Walter NOLL, published by Academic Press.

Polysiloxanes for use in the invention are selected from volatile silicones with a boiling point of between 60° C. and 260° C. or non volatile silicones selected in particular from polyalkylsiloxanes, polyarylsiloxanes, polyalkylarylsiloxanes, silicone gums and resins, organomodified polysiloxanes and mixtures thereof.

Volatile silicones may be selected from:

(i) Cyclic silicones comprising three to seven silicon atoms, preferably four to five. The following are examples: octamethylcyclotetrasiloxane sold by UNION CARBIDE under the trade name VOLATILE SILICONE 7207 or by RHONE POULENC under the trade name SILBIONE 70045 V 2, decamethyl-cyclopentasiloxane sold by UNION CARBIDE under the trade name VOLATILE SILICONE 7158 or by RHONE POULENC under the trade name SILBIONE 70045 V 5, and mixtures thereof.

The following may also be cited: dimetiylsiloxane/methylalkylsiloxane type cyclocopolymers, such as the dimethylsiloxane/methyloctylsiloxane cyclo-copolymer sold by UNION CARBIDE under the trade name VOLATILE SILICONE FZ 3109.

Mixtures of cyclic silicones with organic silicon derivatives may also be used, such as octamethilcyclotetrasiloxane mixed with tetratrimethylsilylpentaerythritol (50/50) and octamethylcyclotetrasiloxane mixed with oxy-1,1'-(hexa-2, 2,2',2,3,3'-trimethylsilyl-oxy)bis-neopentane;

(ii) Linear volatile silicones with two to nine silicon atoms having a viscosity less than or equal to $5.10^{-6}$ m$^2$/s at 25° C. The following are examples: hexamethyldisiloxane sold by RHONE POULENC under the trade name SILBIONE 70 041 V 0.65, decamethyltetrasiloxane sold by TORAY SILICONE under the trade name SH 200, or volatile polymethylphenylsiloxanes such as SILICONOL AS sold by WACKER. Silicones of this type are also described in "Volatile Silicone Fluids for Cosmetics", by TODD & BYERS, Cosmetics and Toiletries, Vol 91, January 1976, p 27–32.

Polyalkylsiloxanes are particularly preferred non volatile silicones, for example linear polydimethylsiloxanes with trimethylsilyl terminal groups, having a viscosity of $5.10^{-6}$ to 2.5 m$^2$/s at 25° C., preferably $10^{-5}$ to 1 m$^2$/s. Non limiting examples are:

SILBIONE oils of series 47 and 70 047 sold by RHONE POULENC, such as oil 47 v 500.000, series 200 oils sold by DOW CORNING, VISCASIL oils sold by GENERAL ELECTRIC and certain SF series oils from GENERAL ELECTRIC (SF 96, SF 18).

Linear polydimethylsiloxanes with dimethylsilanol terminal groups may also be used, such as 48 series oils from RHONE POULENC.

Polydimethylsiloxanes with a viscosity of greater than $10^{-1}$ m$^2$/s are preferred.

In this class of polyalkylsiloxanes, poly($C_1$–$C_{20}$)alkylsiloxane waxes sold by GOLDSCHMIDT under the trade names ABIL WAX 9800 and ABIL WAX 9801 may also be used.

Polyalkylarylsiloxanes which may be used are polydimethylmethylphenylsiloxanes, polymethylphenylsiloxanes, and linear or branched polydimethyldiphenylsiloxanes with a viscosity of $10^{-5}$ to $5.10^{-2}$ $m^2/s$ at 25° C., such as, for example:

RHODORSIL 70 633 and 763 series oils from RHONE POULENC,

SILBIONE oils of series 70 641 from RHONE POULENC,

DC 556 COSMETIC GRADE FLUID oil from DOW CORNING,

PK series silicones, such as PK20, from BAYER,

PN, PH series silicones, such as PN 1000 and PH 1000, from BAYER, some SF series oils, such as SF 1250, SF 1265, SF 1154, SF 1023 from GENERAL ELECTRIC.

Silicone gums in accordance with the invention are polydiorganosiloxanes with high molecular weights of between 200 000 and 1 000 000 used alone or mixed with a solvent selected from volatile silicones such as those defined above, polydimethylsiloxane (PDMS) oils, polyphenylmethylsiloxanes (PPMS), isoparaffins, methylene chloride, pentane, dodecane, tridecane, tetradecane or mixtures thereof.

The following gums may be cited, for example:
poly[(dimethylsiloxane)/(methylvinylsiloxane)],
poly[(dimethylsiloxane)/(diphenylsloxarte)]
poly[(dimethylsiloxane)/(phenylmethylsiloxane)],
poly[(dimethylsiloxane)/(diphenylxiloxane)/methylvinylsiloxane)].

The following mixtures may be cited as non limiting examples:

mixtures formed from a chain end hydroxylated polydimethylsiloxane (DIMETICONOL in accordance with CTFA nomenclature) and a cyclic polydimethylsiloxane (CYCLOMETHICONE in accordance with CTFA nomenclature), such as Q2 1401 sold by DOW CORNING, mixtures formed from a polydimethylsiloxare gum and a cyclic silicone, such as SF 1214 Silicone Fluid from GENERAL ELECTRIC (an SE 30 gum, corresponding to a dimethicone, with a molecular weight of 500 000 dissolved in SF 1202 Silicone Fluid (corresponding to decamethyl-cyclo-pentasiloxane)), mixtures of two PDMS of different viscosities, in particular a PDMS gum and a PDMS oil, such as SF 1236 and CF 1241 from GENERAL ELECTRIC. SF 1236 is a mixture of SE 30 gum as defined above with a viscosity of 20 $m^2/s$ and SF 96 oil with a viscosity of $5.10^{-6}$ $m^2/s$ (15% SE 30 gum and 85% SF 96 oil).

CF 1241 is a mixture of SE 30 gum (33%) and a PDMS (67%) with viscosity $10^{-3}$ $m^2/s$.

Organopolysiloxane resins used in the invention are crosslinked siloxane systems containing $R'_2SiO_{2/2}$, $R'SiO_{3/2}$ and $SiO_{4/2}$ units wherein R' represents a hydrocarbon group with one to six carbon atoms or a phenyl group. Particularly preferred compounds are those where R' represents a low alkyl radical or a phenyl radical.

The following resins may be cited dimethyl/trimethylpolysiloxanes sold under the trade name DOW CORNING 593 or those sold under the trade names SILICONE FLUID SS 4230 and SS 4267 by GENERAL EUECTRIC.

Organomodified silicones are those defined above, comprising one or more organiofunctional groups fixed to the siloxane chain either directly or via a hydrocarbon radical.

Organomodified silicones which may be cited are silicones comprising:

1-polyethyleneoxy and/or polypropyleneoxy groups which may comprise alkyl groups such as:

dimethicone copolyol sold by DOW CORNING under the trade name DC 1248, and ($C_{12}$)alkylmethicone copolyol sold by DOW CORNING under the trade name Q2 5201, SILWET L 722, L 7500, L 77, L 711 oil from UNION CARBIDE, a mixture of dimethicone copclyol and cyclomethicone, such as Q2-30225C sold by DOW CORNING, 2-substituted or unsubstituted amine groups such as GP4 Silicone Fluid and GP 7100 sold by GENESSE or Q2 8220, X2 8200 and DC 929 or Q2 7224 sold by DOW CORNING.

Substituted amine groups are in particular amino ($C_1$–$C_4$) alkyl groups, 3-thiol groups such as GP 72A and GP 71 from GENESSE or SLM 50253/5 from WACKER, 4-carboxylate groups such as those described in European patent EP-A-186 507 (CHISSO CORPORATION), 5-alkoxyl groups such as SILICONE COPOLYMER F-755 from SWS SILICONES and ABIL WAX 2428, 2434 and 2440 from GOLDSCHMIDT, 6-hydroxyl groups such as polyorganosilcxanes with hydroxyalkyl functional groups described in French patent FR-A-85 16 334 and having the following formula (I):

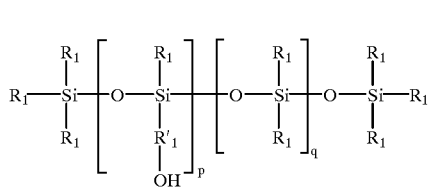

wherein:

radicals $R'_1$, which may be identical or different, are selected from methyl and phenyl radicals, aet least 60 mole % of radicals $R_1$ designating methyl;

radical $R'_1$ is a divalent hydrocarbonated $C_2$–$C_{18}$ alkylene link;

p is between 1 and 30 inclusive;

q is between 1 and 150 inclusive.

A polyorganosiloxane of this type is sold by RHONE POULENC under the trade name 71615 V 300, for example.

7-acyloxyalkyl groups such as polyorganosiloxanes described in French patent application FR-A-2 641 185 having formula (II):

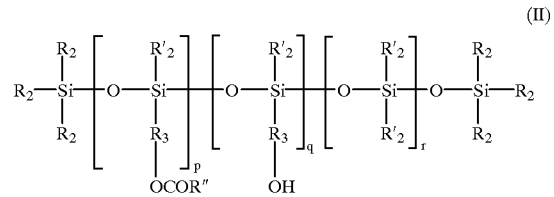

wherein:

$R_2$ represents a methyl phenyl, —OCOR" or hydroxyl group where only one radical $R_2$ per silicon atom may be OH;

$R'_2$ represents methyl or phenyl, at least 60 mole % of the total of radicals $R_2$ and $R'_2$ representing methyl;

R" represents a $C_8$–$C_{20}$ alkyl or alkenyl;

$R_3$ represents a divalent hydrocarbonated linear or branched $C_2$–$C_{18}$ alkylene radical;

r is between 1 and 120 inclusive;

p is between 1 and 30;

q is zero or less than 0.5p, p+q being between 1 and 30;

polyorganosiloxanes of formula (II) may contain

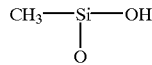

groups in proportions not exceeding 15% of the sum p+q+r.

8- carboxylic type anionic groups such as those in the product X-22-3701E from SHIN-ETSU or in the product Silicone Fluid FZ 3703 from UNION CARBIDE; 2-hydroxy-alkylsulfonate; or 2-hydroxyalkylthiosulfate such as ABIL S201 and ABIL S255 from GOLDSCHMIDT.

Particularly preferred polyorganosiloxanes for use in the invention are;

silicone oils with a high viscosity of between 0.2 and 2.5m²/s at 25° C. such as 47 V 500.000 oils from RHONE POULENC, mixtures of organopolysiloxanes and cyclic silicones such as Q2 1401 from DOW CORNING, mixtures of two PDMS with differing viscosities such as CF 1241 sold by GENERAL ELECTRIC.

The latexes used are colloidal suspensions of polymer particles in an aqueous liquid phase. These latexes are normally obtained by polymerization or copolymerization of monomers in suspension or emulsion using techniques which are well known in the art.

Latexes used in the invention are preferably formed by polymerization or copolymerization of monomers such as styrene, butadiene, acrylonitrile, chloroprine, vinyl acetate, urethanes, isoprene, isobutylene, and acrylic, methacrylic maleic, crotonic, or itaconic acid or their esters or amides.

The latexes are insoluble in aqueous media and must also possess film forming and restructuring properties.

In accordance with the invention, a latex is film forming if 100 ml of a solution of 8 g/100 ml placed on a strictly horizontal matrix with a surface area of 65 cm² can be seen with the naked eye to have produced a fine, homogeneous film over the entire surface of the matrix after 15 hours drying at room temperature.

A latex is restructuring if on application to the hair surface it restores the fibre to its original shape. The term restructuring is not used to describe any modification to the keratin itself.

Particularly preferred latexes for use in the invention are:

homopolymers and copolymers of vinyl acetate such as:

vinyl polyacetate such as RHODOPAS A012P emulsion and RHODOPAS A013P emulsion sold by RHONE POULENC;

copolymers of vinyl acetate and ethylene such as APPRETAN MB, APPRETAN EM and APPRETAN TV from HOECHST;

homopolymers or copolymers derived from acrylic acid such as PRIMAL AC-33, PRIMAL K-3, PRIMAL TR-93, PRIMAL HA-8, and PRIMAL E-358 sold by ROHM & HAAS or RHODOPAS SD215 sold by RHONE POULENC;

polyurethanes such as WITCOBOND 160 sold by WITCO;

carboxylated or uncarboxylated butadiene/styrene copolymers such as RHODOPAS SB02 emulsion, RHODOPAS ST246 emulsion, RHODOPAS SB153 emulsion and RHODOPAS GB012 emulsion from RHONE POULENC;

butadiene/acrylonitrile copolymers, carboxylated or uncarboxylated, such as HYCAR 1562 from GOODRICH and CHEMIGUM L6271 from GOODYEAR;

styrene/acrylic ester copolymers such as APPRETAN V3749 from HOECHST.

Concerning the thickening agents, this ammonium acrylate/acrylamide copolymer is crosslinked in aqueous medium using a polyunsaturated olefinic crosslinking agent and dispersed in a water-in-oil emulsion comprising paraffin and a mixture of sorbitan stearite and a hydrophilic ethoxylated derivative. It is preferred to use the emulsion sold by HOECHST under the trade name PAS 5161 which comprises ammonium acrylate/acrylamide copolymer (95/5 by weight), the medium being constituted by 30% by weight of said polymer, 25% by weight of paraffin, 4% of the mixture of sorbitan stearate and hydrophilic ethoxylated derivative and 41% water.

The suspension agents are selected from compounds with formula:

a) $R_4X$                                                      (III)

wherein $R_4$ is a long carbon chain aliphatic radical which may include oxygen atoms and X is a carboxylic, sulfuric or phosphoric acid residue or a radical derived from a carboxylic acid or an amide; the compounds of formula (III) are selected from those wherein:

(i) $R_4$ is a $C_{11}$–$C_{21}$, alkyl or alkenyl radical, X is:

a COOA group wherein A is a mono- or polyhydroxyalkyl $C_2$–$C_3$ polyol derivative or a $CH_2CH_2SO_3M$ radical, a $CO(OCH_2CH_2)_n$-OH group wherein n is between 2 and 150,

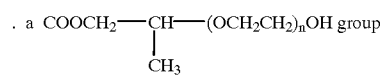

wherein n is between 2 and 150, the free OH groups of the groups defined above possibly being esterified using an acid $R_4COOH$ where $R_4$ is a $C_{11}$–$C_{21}$ alkyl or alkenyl group, a $CONR_5R_6$ group wherein $R_5$ or $R_6$ represent hydrogen or $C_1$–$C_4$ hydroxyalkyl, one at least representing $C_1$–$C_4$ hydroxyalkyl, a $OSO_3M$ or $⅓\ PO_4^{3\ominus}M_3$ group wherein M represents an alkali metal, ammonium or a $C_1$–$C_4$ alkanolamine residue;

(ii) $R_4$ represents a $R_7(OC_2H_4)_1OCH_2$ radical and X represents a COOM group wherein M has the meaning given above, $R_7$ representing a $C_{12}$–$C_{14}$ alkyl radical and 1 a whole or decimal number between 2.5 and 10, or $R_7$ represents oleyl and 1 is between 2 and 9 or $R_7$ represents ($C_8$–$C_9$)alkylphenyl and 1 is between 4 and 8, or derivatives wherein $R_4$ represents a ($C_{12}$–$C_{16}$) alkyl alkyl group and X represents a $CONR_5R_6$ group wherein $R_5$ and $R_6$ have the meanings given above;

b) oxides of dimethyl ($C_{16}$–$C_{22}$)alkylanines.

A further suspension agent for use in the invention is an alcohol having 27 to 44 carbon atoms and comprising one or more ether and/or thioether or sulfoxide groups with formula (IV):

$R_8$—X—[$C_2H_3(OH)$]—$CH_2$—Y—$R_9$                   (IV)

wherein;

$R_8$ and $R_9$, which may be identical or different, represent linear $C_{12}$–$C_{20}$ alkyl groups;

X represents an oxygen atom, a sulfur atom or a sulfoxide group;

Y represents an oxygen atom, a sulfur atom, a sulfoxide group or a methylene group; when Y represents a methylene group the sum of the number of carbon atoms in $R_8$ and $R_9$ is from 24 to 40, preferably from 26 to 36 inclusive and when Y does not represent a methylene group the sum of the carbon atoms in $R_8$ and $R_9$ is from 24 to 40 inclusive, preferably from 28 to 36 inclusive; when X or Y represents sulfoxide Y or X does not represent sulfur.

Preferred compositions in accordance with the invention contain an insoluble silicone such as the mixture formed from a chain end hydroxylated polydimethylsiloxane, denominated DIMETHICONOL in accordance with CTFA nomenclature, and a cyclic polydimethylsiloxane denominated CYCLOMETHICONE in accordance with CTFA nomenclature, a latex which is a homopolymer or a copolymer derived from acrylic acid, the composition preferably containing as thickening agent an aqueous dispersion of crosslinked ammonium acrylate and acrylamide copolymer defined above.

The silicone(s) used in compositions in accordance with the invention are in proportions of between 0.1 and 50% by weight with respect to the total composition weight, preferably 0.2 to 30% by weight; the latex is preferably present in proportions of between 3.1 and 10% by weight, in particular between 0.5 and 5% by weight; the thickening agent or suspension agent is used in proportions sufficient to thicken or put into suspension the silicone(s) or latex(es), the proportions being preferably between 0.1 and 20% by weight, in particular between 0.3 and 10% by weight with respect to the total composition weight.

Compositions in accordance with the invention may contain various additives depending on the intended use.

When the compositions are used as a shampoo they also contain anionic, non-ionic, amphoteric or zwitterionic surfactant detergents or mixtures thereof in proportions of between 5 and 50% by weight, preferably between 8 and 35% by weight with respect to the total composition weight.

Treatment compositions may also contain polymers other than latex, in particular cosmetically acceptable polymers, proteins, these polymers being selected and used in proportions which do not affect composition stability.

Compositions in accordance with the intention may also contain other additives which are frequently used in cosmetics such as perfumes, preservatives, sequestrating agents, foam stabilisers, propellants, dyes, acidifying or alkalising agents, depending on the intended use.

When the compositions are intended for therapeutic use, for example for hair or skin, they also contain active substances for treating dermatological complaints or the hair.

Compositions in accordance with the invention may also be used as a rinsed or non-rinsed treatment lotion for application before or after shampooing, before or after perming, before or after dyeing or bleaching or between two perming or straightening steps.

Compositions in accordance with the invention may also be used in eye makeup, in particular in mascara. In this case, they may also contain pigments, animal, vegetable or mineral oils or waxes, fatty alcohols fatty acid esters or fatty acids. These composition are easy to apply uniformly and last well.

A treatment method in accordance with the invention consists in applying the composition defined above to the keratinous material in proportions sufficient to repair the hair fibres and produce the required softness and combthrough properties. When used as a shampoo, the composition is applied to wet hair and left for a few minutes and then the hair is rinsed and dried.

The following are non limiting examples which illustrate the invention.

EXAMPLE 1

A non-rinse conditioner was prepared as follows:

Mixture of octamethylcyclotetrasiloxane dimethiconol (13%) and dodecamethylcyclopentasiloxane (87%) sold by DOW CORNING under the trade name Q2 1401 20.0 g Aqueous dispersion of vinyl polyacetate sold at 54% AM by RHONE POULENC under the trade name RHODOPAS A 012P Emulsion 1.0 g AM Emulsion of crosslinked ammonium acylate/acrylamide copolymer sold by HOECHST under the trade nane PAS 5161 0.3 g AM Preservative, perfume qs Hydrochloric acid qs pH=6

Water qsp 100.0 g

EXAMPLE 2

A rinsed conditioner having the following composition was prepared:

Mixture of two PDMS of differing viscosities sold by GENERAL ELECTRIC under the trade name CF 1241 3.0 g Aqueous emulsion of polyurethane sold at 35% AM by WITCO under the trade name WITCOBOND 160 1.8 g AM O/W emulsion of acrylamide/sodium 2-methyl-propanesulfonate acrylamide copolymer, sold at 35–45% AM by SEPPIC under the trade name SEPIGEL 305 1.5 g AM Preservative, perfume gs Hydrochloric acid qs pH=8

Water qsp 100.0 g

EXAMPLE 3

A rinsed conditioner having the following composition was prepared:

Polydimethylsiloxane sold by RHONE POULENC under the trade name 47 V 500.000 oil 2.0 g Aqueous dispersion of butacdiene/acrylo-nitrile copolymer sold at 41% AM by GOODRICH under the trade name HYCAR 1562 5.0 g AM Sodium alginate sold by SOCIETE FRANCAISE DES COLLOIDES under the trade name ALGINATE MP/8 4.0 g Preservative, perfume qs Hydrochloric acid qs pH=7

Water qsp 100.0 q

EXAMPLE 4

A rinsed conditioner having the following composition was prepared:

polydinethylsiloxane sold by RHONE POULENC under the trade nane 47V 500.000 oil 20.0 g Aqueous acrylic emulsion sold at 46% AM by ROHM & HAAS under the trade name PRIMAL HA 8 0.5 g AM
Guar gum 2.0 g
Preservative, perfume qs
Sodium hydroxide qs pH=6
Water qsp 100.0 g

EXAMPLE 5

A non-rinsed conditioner having the following composition was prepared:
polydimethylsiloxane sold by RHONE POULENC under the trade name 47V 500.000 oil 5.0 g
Aqueous dispersion of self-crosslinking styrene/acrylic ester copolymer, sold by HOECHST under the trade name APPRETAN V 3749 10.0 g
Crosslinked polyacrylic acid, sold by GOODRICH under the trade name CARBOPOL 940 0.9 g
Preservative qs
Triethanolamine qs pH=4.2
Water qsp 100.0 g

EXAMPLE 6

A shampoo having the following composition was prepared:
Sodium laurylethersulfate oxyethylenated with 2 moles ethylene oxide at 28% AM 16.8 g AM
Cocoylbetain at 32% AM 2.6 g AM
Compound of formula (IV) wherein: $R_8$ represents $C_{16}H_{33}$ $R_9$ represents $C_{14}H_{29}$ X represents O Y represents $CH_2$ prepared by reacting 3 moles of alcohol with 1 mole epoxide, used unpurified 2.5 g
Mixture of isopropanolamides of copra acid sold by MARCHON under the trade name EMPILAN CIS 1.0 g
Lanette wax 0.75 g
Polydimethylsiloxane sold by RHONE POULENC under the trade name 47 V 500.000 oil 3.0 g
Aqueous acrylic emulsion sold by ROHM & HAAS under the trade name PRIMAL K-3 3.0 g
Preservative, perfume qs
Spot pH=5.1
Water qsp 100.0 g

EXAMPLE 7

A non-rinsed conditioner having the following composition was prepared:
O/W emulsion of acrylamide/sodium 2-methyl-propanesulfonate acrylamide copolymer sold at 35–45% AM by SEPPIC under the trade name SEPI-GEL 305 0.8 g AM
Latex of vinyl acetate/acrzrlic ester copolymer sold at 54% AM by RHONE POULENC under the trade name RHODOPAS AD 310 1.0 g AM
Mixture of octamethylcyclotetrasiloxane dimethiconol (13%) and dodecamethylcyclopentasiloxane (87%) sold by DOW CORNING under the trade name Q2 1401 20.0 g
Preservative qs
Spot pH=4.9
Water qsp 100.0 g

EXAMPLE 8

Mascara
Triethanolamine stearate 13.0 g
Beeswax 12.0 g
Candelilla wax 3.0 g
Emulsion of crosslinked ammonium acrylate/acrylamide copolymer sold by HOECHST under the trade name PAS 5161 0.15 g
Gum arabic 1.0 g
Polyvinylpyrrolidone 1.0 g
Acrylic ester/styrene copolymer in anionic dispersion at 50% sold by RHONE POULENC under the trade name RHODOPAS SD 215 4.0 g
Black iron oxides 7.0 g
Mixture of dimethiconol and cyclomethicone sold by DOW CORNING under the trade name SILICONE Q2 1401 5.3 g
Preservatives 0.4 g
Water qsp 100.0 g The oily phase was heated to 85° C. and the iron oxides were added. The aqueous phase containing the various hydrosoluble compounds was heated to 35° C. The aqueous phase was added to the oily phase with vigorous stirring in an effuser. The silicone mixture was added at 60° C. and the mixture was allowed to cool to room temperature.

This mascara was easy to apply to the lashes and produced a durable, uniform makeup.

We claim:

1. A composition for treatment of keratinous materials, consisting essentially of in an aqueous medium, at least one silicone, at least one latex consisting of a colloidal suspension of polymer particles insoluble in said aqueous medium, and at least one suspension agent for the silicone and the latex and/or at least one thickening agent selected from the group consisting of guar gum, gum arabic, scleroglucanes, polyacrylic acids which are crosslinked or non-crosslinked, aqueous dispersions of crosslinked ammonium acrylate/acrylamide copolymers and an emulsion of neutralised acrylamide/2-methylpropane sulfonic acrylamide copolymer.

2. Composition according to claim 1 wherein the silicone is selected from the group consisting of polyorganosiloxanes which are soluble or insoluble in the aqueous medium and are in a form selected from the group consisting of an oil, a wax, a gum and a resin.

3. Composition according to claim 2 wherein the polyorganosiloxanes are selected from the group consisting of volatile silicones.

4. Composition according to claim 3 wherein the volatile silicones are selected from the group consisting of:
cyclic silicones comprising three to seven silicon atoms;
dimethylsiloxane/methylalkylsiloxane cyclopolymers;
mixtures of cyclic silicones with organic silicon derivatives; and
linear volatile silicones having two to nine silicon atoms and a viscosity less than or equal to $5.10^{-6} m^2/s$ at 25° C.

5. Composition according to claim 1 wherein the silicones are non-volatile silicones selected from the group consisting of:
(a) polyalkylsiloxanes selected from the group consisting of:
linear polydimethylsiloxanes having trimethylsilyl terminal groups and a viscosity of between $5.10^{-6}$ and $2.5 \ m^2/s$ at 25° C.

linear polydimethylsiloxanes with dimethylsilanol terminal groups; and
poly ($C_1$–$C_{20}$)alkylsiloxanes;
(b) polyalkylarylsiloxanes selected from the group consisting of:
polydimethylmethylphenylsiloxanes, polymethylphenylsiloxanes and linear and branched polydimethyldiphenylsiloxanes having a viscosity of between $1.10^{-5}$ and $5.10^2$ m$^2$/s at 25° C.;
(c) silicone gums selected from the group consisting of polydiorganosiloxanes having molecular weights of between 200,000 and 1,000,000 used alone or mixed with a solvent;
(d) silicone resins containing the following units:

wherein R' represents a hydrocarbon group having one to six carbon atoms or a phenyl group; and
(e) organomodified silicones selected from the group consisting of silicones comprising one or more organofunctional groups fixed to the siloxane chain directly and via a hydrocarbon radical.

6. Composition according to claim 5 wherein the silicone gums used either alone or in a mixture are selected from the group consisting of:
poly[(dimethylsiloxane)/(methylvinylsiloxane)],
poly[(dimethylsiloxane)/(diphenylsiloxane)],
poly[(dimethylsiloxane)/(phenylmethylsiloxane)],
poly[(dimethylsiloxane)/(diphenylsiloxane)/(methylvinylsiloxane)]
and the following mixtures:
mixtures formed from a chain end hydroxylated polydimethylsiloxane and a cyclic polydimethylsiloxane;
mixtures formed from a polydimethylsiloxane gum and a cyclic silicone; and
mixtures of polydimethylsiloxane in which the polymethylsiloxanes have different viscosities.

7. Composition according to claim 5 wherein the organomodified silicones are selected from the group consisting of the following polyorganosiloxanes:
a) polyethyleneoxy and polypropyleneoxy groups;
b) substituted and unsubstituted amine groups;
c) thiol groups;
d) carboxylate groups
e) alkoxyl groups;
f) hydroxyalkyl groups having the following formula:

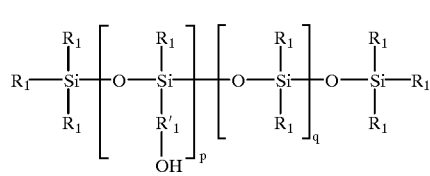

(I)

wherein:
radicals $R_1$, which may be identical or different, are selected from the group consisting of methyl and phenyl radicals, at least 60 mole % of radicals $R_1$ designating methyl;

radical R', is a divalent hydrocarbonated $C_2$–$C_{18}$ alkylene link;
p is between 1 and 30 inclusive;
q is between 1 and 150 inclusive;
g) acyloxyalkyl groups having the following formula:

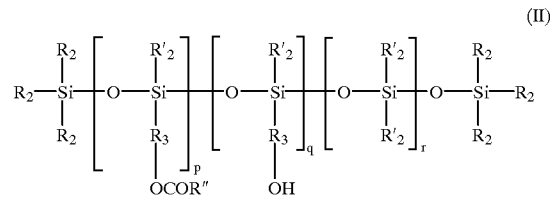

(II)

wherein:
$R_2$ represents a methyl, phenyl, —OCR" or hydroxyl group where only one radical $R_2$ per silicon atom is OH;
$R'_2$ represents methyl or phenyl, at least 60 mole % of the total of radicals $R_2$ and $R'_2$ representing methyl;
R" represents a $C_8$–$C_{20}$ alkyl or alkenyl group;
$R_3$ represents a divalent hydrocarbonated alkylene linear $C_2$–$C_{18}$ radical or branched $C_2$–$C_{18}$ radical;
r is between 1 and 120 inclusive;
p is between 1 and 30;
q is zero or less than 0.5 p, p+q being between 1 and 30;
polyorganosiloxanes of formula (II) optionally containing

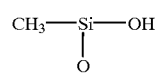

groups in proportions not exceeding 15% of the sum p+q+r;
h) alkylcarboxyl groups;
i) 2-hydroxyalkylsulfonate groups; and
j) 2-hydroxyalkylthiosulfate groups.

8. Composition according to claim 2 wherein the polyorganosiloxanes are selected from the group consisting of linear polyalkylsiloxanes with trimethylsilyl terminal groups and a viscosity of between 0.2 and 2.5 m$^2$/s at 25° C., mixtures of a chain end hydroxylated polydimethylsiloxane and a cyclic polydimethylsiloxane and mixtures of two polydimethylsiloxanes constituted by a gum and an oil wherein the gum and oil have different viscosities.

9. Composition according to claim 1 wherein the latex is a colloidal suspension of polymer particles obtained by polymerization or copolymerization of monomers selected from the group consisting of styrene, butadiene, acrylonitrile, chloroprene, vinyl acetate, urethanes, isoprene, isobutylene and acrylic, methacrylic, maleic, crotonic and itacronic acid and their esters or amides.

10. composition according to claim 9 wherein the latex which is insoluble in the aqueous medium is selected from the group consisting of homopolymers and copolymers of vinyl acetate, homopolymers and copolymers of acrylic acid, polyurethanes, carboxylated and non-carboxylated butadiene/styrene copolymers, carboxylated and non-carboxylated butadiene/acrylonitrile copolymers and styrene/acrylic ester copolymers.

11. Composition according to claim 1 wherein the suspension agent is selected from the group consisting of compounds having the formula:

a) $R_4X$  (III)

wherein $R_4$ is a long carbon chain aliphatic radical which may optionally include oxygen atoms and X is selected from the group consisting of a carboxylic, sulfuric and phosphoric acid residue and a radical derived from a carboxylic acid and a radical derived from an amide.

12. Composition according to claim 1 wherein the suspension agent is an alcohol having 27 to 44 carbon atoms and including one or two ether and/or thioether or sulfoxide groups and has the formula (IV):

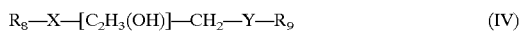

wherein:

$R_8$ and $R_9$, which may be identical or different, represent linear $C_{12}$–$C_{20}$ alkyl groups;

X represents an oxygen atom, a sulfur atom or a sulfoxide group;

Y represents an oxygen atom, a sulfur atom, a sulfoxide group or a methylene group; when Y represents a methylene group the sum of the number of carbon atoms in $R_8$ and $R_9$ is from 24 to 40, and when Y does not represent a methylene group the sum of the carbon atoms in $R_8$ and $R_9$ is from 24 to 40 inclusive when X or Y represents sulfoxide, Y or X does not designate sulfur.

13. Composition according to claim 1 wherein the composition comprises a mixture of a chain end hydroxylated polydimethylsiloxane and a cyclic polydimethylsiloxane, a latex which is a homopolymer or copolymer derived from acrylic acid and a thickening agent which is a crosslinked ammonium acrylate and acrylamide copolymer.

14. Composition according to claim 1 wherein the silicone(s) are present in proportions of between 0.1 and 50% by weight with respect to the total composition weight.

15. Composition according to claim 1 wherein the latex is present in the composition in proportions of between 0.1 and 10% by weight with respect to the total composition weight.

16. Composition according to claim 1 wherein the thickening agent and/or suspension agent are present in the composition in proportions of between 0.1 and 20% by weight with respect to the total composition weight.

17. Composition according to claim 1 wherein it is in the form of a shampoo containing at least one surfactant detergent selected from the group consisting of anionic, nonionic, amphoteric and zwitterionic surfactants and mixtures thereof.

18. Method of treating keratinous material wherein at least one composition as defined in claim 1 the keratinous material.

19. A composition as defined in claim 17 as in the form of a shampoo.

20. A composition as defined in claim 1 in the form of a mascara.

21. A composition for treatment of keratinous materials consisting essentially of, in an aqueous medium, at least one silicone, at least one latex consisting of a colloidal suspension of polymer particles consisting essentially of acrylic acid containing polymers insoluble in said aqueous medium, and at least one suspension agent for the silicone and the latex and/or at least one thickening agent which is an aqueous dispersion of crosslinked ammonium acrylate/acrylamide copolymers.

* * * * *